United States Patent [19]
Pruyssers

[11] Patent Number: 5,443,444
[45] Date of Patent: Aug. 22, 1995

[54] ORTHOPAEDIC POLYCENTRIC HINGE

[75] Inventor: Adriaan C. Pruyssers, Encinitas, Calif.

[73] Assignee: Professional Care Products Incorporated, Vista, Calif.

[21] Appl. No.: 276,935

[22] Filed: Jul. 19, 1994

[51] Int. Cl.⁶ .............................................. A61F 5/00
[52] U.S. Cl. ........................................ 602/26; 602/5; 602/16
[58] Field of Search .................... 602/16, 26, 27, 5, 20, 602/23

[56] References Cited

U.S. PATENT DOCUMENTS

| | | |
|---|---|---|
| 401,933 | 4/1889 | DeCamp . |
| 3,817,244 | 6/1974 | Taylor . |
| 3,901,223 | 8/1975 | May . |
| 4,372,298 | 2/1983 | Lerman . |
| 4,493,316 | 1/1985 | Reed et al. . |
| 4,628,916 | 12/1986 | Lerman et al. . |
| 4,697,583 | 10/1987 | Mason et al. . |
| 4,726,361 | 2/1988 | Farley . |
| 4,732,143 | 3/1988 | Kausek et al. . |
| 4,777,941 | 10/1988 | Borig et al. ............. 602/16 |
| 5,022,391 | 7/1991 | Weidenburner ............. 602/26 X |
| 5,038,763 | 8/1991 | Wiggins . |
| 5,042,464 | 8/1991 | Skwok et al. ............. 602/26 X |
| 5,060,640 | 10/1991 | Rasmusson ............. 602/26 X |
| 5,062,858 | 11/1991 | Broeck et al. ............. 602/16 X |
| 5,078,127 | 1/1992 | Daneman et al. . |
| 5,230,696 | 7/1993 | Silver et al. ............. 602/26 X |
| 5,292,303 | 3/1994 | Bastyr et al. ............. 602/16 |
| 5,330,418 | 7/1994 | Townsend et al. ............. 602/26 |
| 5,356,370 | 10/1994 | Fleming ............. 602/26 X |

FOREIGN PATENT DOCUMENTS

| | | |
|---|---|---|
| 1187444 | 9/1959 | France . |
| 1316572 | 5/1973 | United Kingdom . |
| 2265087 | 9/1993 | United Kingdom . |

*Primary Examiner*—Richard J. Apley
*Assistant Examiner*—Kim M. Lee
*Attorney, Agent, or Firm*—Juettner Pyle Lloyd & Piontek

[57] ABSTRACT

A polycentric hinge for orthopaedic braces includes a pair of rigid support arms having cooperating, interlocking proximal ends, a pair of pivot pins and a hinge plate. The arms are rotatably coupled at their proximal ends to the hinge plate through the pivot pins and are rotatable between an adjustable extension position and an adjustable flexion position. The hinge plate has a plurality of adjustment apertures therein adapted for selective reception of an extension limit pin and a flexion limit pin to selectively restrain rotation of the arms beyond a final extension position and a final flexion position. The pins are secured to the hinge assembly by elastomeric tethers and are positionable between the apertures to selectively adjust the range of motion of the arms. A flip-top cap covers the pins to prevent inadvertent displacement of the pins from the selected apertures.

10 Claims, 8 Drawing Sheets

ORTHOPAEDIC POLYCENTRIC HINGE

FIELD OF THE INVENTION

The present invention relates to an improved orthopaedic articulating brace, and more particularly, to an orthopaedic polycentric hinge having mutually engaging rigid support arms and means for conveniently adjusting the range of motion permitted between the arms.

BACKGROUND OF THE INVENTION

The human knee joint provides for relative articulation of the upper and lower legs, between the femur and tibia, through a plurality of centers or axes over an arc of about 180°. To effectively duplicate the movement of the human knee joint when necessary to mechanically assist the knee, for example, following injury or a surgical procedure, the art has developed articulated knee supporting braces embodying plural axis or polycentric hinges worn about the knee of the patient, these hinges may be used to support the knee joint throughout its full range of motion, or to lock the knee joint in a selected position, or to limit the allowed range of motion of the joint to less than compete extension (straightening) and/or to less than complete flexion (bending) of the knee. During rehabilitation, it is common to initially limit articulation of the knee and to progressively increase the permitted range of motion in gradual increments as healing progresses.

Examples of prior art developments in knee braces may be found in U.S. Pat. Nos. 5,292,303 to Bastyr et al., 401,933 to De Camp, 5,062,858 to Broeck et al., 4,732,143 to Kausek et al., 5,038,763 to Wiggins, 4,726,361 to Farley, 4,628,916 to Lerman et al., 3,817,244 to Taylor, 3,901,223 to May, 4,372,298 to Lerman, 4,493,316 to Reed et al., and in British Patent No. 1,316,572 and French Patent No. 1,187,444, among others. Some of these patents disclose knee braces with polycentric hinges and others have hinges with a single axis of rotation.

As an example of a hinge having a single axis of rotation, Bastyr et al. discloses an orthopaedic brace having a pair of arms joined through a hinge having a pair of hinge plates and a single pivot pin, about which the arms pivot relative to each other. Limit pins selectively insertable within angularly and radially spaced apart holes in the hinge plates adjustably limit the pivotal motion between the arms. Each limit pin is retained in association with the hinge pivot pin by a retention member provided with a slot in one end to movably retain the pin during repositioning of the pin among the holes. The opposite end of the retention member is pivotally mounted on the hinge pivot pin. A cover with a lid allows selective access to the pins and enables repositioning of the pins as desired.

A further example of a device having a single axis of rotation is De Camp, which discloses a surgeons' splint having a pair of arms overlappingly attached at their adjacent ends by a rivet to form a hinge-joint. A segment of a disc located between the adjacent arm ends has a center opening for receiving the rivet and a series of openings arranged concentrically about the pin. The openings are adapted to selectively receive a pair of stop pins attached to and held in place by a corresponding pair of flexible retaining springs pivotally mounted on the hinge pin rivet. The stop pins are capable of restricting angular rotation of the hinge-joint to a desired range of motion or entirely locking up the hinge-joint.

An example of a polycentric knee brace hinge is disclosed in Broeck et al., wherein a pair of juxtaposed joint members having mutually engaging toothed sectors at their adjacent ends are pivotally mounted on respective ones of a pair of spaced, parallel tubular pivot pins. The pivot pins extend between and pivotally mount the adjacent ends of the joint members between two parallel spaced apart side plates. The side plates have openings therein spaced angularly about each of the tubular pivot pins. Rigid stops are provided for insertion into the openings to limit rotation of the joint members about the pivot pins. Each of the stops includes a rod insertable into one of the openings and an integral plate extending parallel to the side plates and mounted on a respective one of the pivot pins. Each stop plate is in turn retained on the respective pivot pin by a securing pin removably inserted into the hollow pivot pin. Repositioning of each of the stops is accomplished by removal of the securing pin from the tubular pivot pin, withdrawal of the stop rod from a hole, reinsertion of the rod into another hole, realignment of the plate with the pivot pin, and reattachment of the securing pin.

Although capable of providing adjustable polycentric rotation and allowing loading to be shared by the adjacent ends of the hinge members as well as the pivot pins and hinge plates, Broeck et al.'s mode of adjustment is complicated and time consuming and there is no means to prevent loss or misplacement of the securing pins and/or limit stops during the adjustment process. Lerman et al. '916 discloses rigid upper and lower support arms juxtaposed to one another at their lower and upper ends respectively, a first hinge bar pivotally connected to the adjacent or proximal ends of the two arms and extending diagonally between them on one side of the two arms, and a second hinge bar pivotally connected to the proximal ends of the two arms at the other side of the two arms and extending diagonally between them in the opposite direction to the first bar, so that the two hinge bars describe an X-shaped hinge system having four pivot axes, i.e., one adjacent each edge of each hinge bar. The two hinge bars allow relative rotation of the support arms in a plural axis motion approximating that of the human knee. The proximal or adjacent ends of the arms are configured to rotate into abutting, but not interlocking, relationship when they are in their upright position, i.e., with the arms aligned in a substantially straight line, in order to prohibit rotation beyond the upright position and thereby prevent hyperextension of the knee.

In the Lerman et al. '916 hinge, the proximal ends of the two arms are tapered away from one another in the direction of rotation opposite the upright position in order to accommodate a full 180° of movement between the arms, i.e., from the upright position wherein the arms are aligned to a position where the arms are parallel to one another in side by side relationship. The hinge thus accommodates complete extension and complete flexion of the knee joint. However, movement of the support arms from complete extension toward complete flexion results in development of a progressively widening tapered open space between the proximal ends of the arms so that the arms are no longer in contact with one another and the hinge bars and pivot pins must carry the entirety of the stress imposed upon the knee and the supporting brace. Thus, the loads which may be safely imposed on the hinge are limited to those supportable by only the pivot pins and hinge bars.

Kausek et al. discloses a hinge for preventing hyperextension including a pair of arms connected by a polycentric hinge. The hinge includes a removable extension stop for limiting the forward pivotal movement of the arms, the extension stop being shaped to cooperate with a set of flanges on each of the arms to physically interfere with further extension. However, in Kausek et al., only a single final extension angle can be predetermined by use of an extension stop. Multiple sized extension stops, as separate pieces, are required to accommodate different final extension angles. Moreover, as separate pieces, there is no means to prevent the loss of one or more of the extension stops.

Wiggins discloses a polycentric hinge having upper and lower brace members coupled through upper and lower pivots by an interleaved link member. The proximal ends of the brace members include gear means engaging each other to cause simultaneous rotation of the brace members about their pivots. By placing the pivots anterior to the knee joint, the rotation of the lower brace tracks the patient's tibia in flexion. Adjustment of the range of motion in extension is accomplished by placing a set screw in abutting relation with the link member, the set screw being disposed within a slot on the lower or proximal end of the upper brace member. The flexion range of motion is adjusted by a cam and screw arrangement also mounted in a slot in the upper brace member. However, the lateral strength and stability of the hinge of Wiggins is limited, as is the hinge's adjustability.

A prior art device, commercially distributed by Professional Care Products, Inc., assignee of the present invention, comprises a pair of support arms and an X-shaped hinge system pivotally interconnecting the adjacent or proximal ends of the support arms for relative rotation about a polycentric axis, duplicating the knee action of the human knee.

The proximal end surfaces of the two arms engage one another, thereby to gain support and guidance from one another, substantially throughout the entirety of an arc of relative rotation from a position of essentially complete extension to a position of essentially complete flexion of the knee. This is accomplished by providing at the proximal ends of the arms complementary, mutually engaging, generally elliptical surfaces formed on an arc of curvature conforming to the polycentric movement accommodated by the X-shaped hinge system. These surfaces are provided with complementary sets of gear teeth which are intermeshed with one another throughout the complete arc of relative rotation of the arms, from the position of nearly complete extension to the position of complete flexion, thereby maintaining a predetermined interengaged relationship between the cooperating parts of the hinge, especially the two support arms. However, adjustment of the permitted degree of extension and/or flexion is very limited.

While all of these prior art orthopaedic hinge devices have their respective advantages, they also have their respective drawbacks or disadvantages.

SUMMARY OF THE INVENTION

The object of the present invention is to provide an improved orthopaedic polycentric hinge especially for knee braces having the advantages but not the shortcomings of the prior art.

One object of the invention is to provide a polycentric hinge where the proximal ends of the rigid support arms remain in continual engagement with one another so that the two arms reinforce and gain support from one another, and the hinge pins are not required to bear the entire weight or stress placed on the brace.

Another object of the invention is to provide a hinge system incorporating an interlocking engagement between the proximal ends of the rigid support arms so they are always maintained in predetermined relation to one another.

A further object of the present invention is to provide an assembly wherein the proximal end portions of the support arms are continually covered to prevent the introduction between them of foreign objects and/or the pinching of the wearer's skin.

An additional object of the invention is to provide a polycentric hinge capable of being conveniently and reliably adjusted and having a wide range of adjustment positions over the full range of motion between complete extension and complete flexion, thereby to provide the proper support and desired degree of articulation while limiting stress to the impaired joint.

Still another object of the invention is to provide a polycentric hinge having means for securely retaining all adjustment members in association with the hinge to prevent accidental loss or misplacement, while maintaining convenience of adjustment.

Yet another object of the invention is to provide an extremely durable hinge having high strength, minimal complexity and low weight, which can be economically fabricated primarily from sheet metal stock with minimal subsequent machining and at a reasonable cost.

In accordance with the invention, an improved polycentric hinge for orthopaedic braces comprises two rigid support arms having cooperating, interlocking, continuously abutting proximal ends rotatably connected to one another by a polycentric hinge assembly including a pair of pivot pins and a hinge plate. Each rigid support arm is rotatably coupled at its proximal end to the hinge plate by a respective one of the pivot pins.

The two arms are pivotable about their respective pivot pins along equal arcs of movement between an adjustable extension position and an adjustable flexion position. The total range of motion of the hinge is from substantially complete extension to substantially complete flexion; the rigid support arms being positioned in substantially straight-line end to end relationship in the complete extension position and being positioned in substantially side by side relation in the complete flexion position. Thus, the hinge accommodates relative angular movement of the rigid support arms substantially between 0° and 180°.

The proximal ends of the arms also include complementary and interlocking arcuate surfaces physically and mutually engaged with one another throughout substantially the entirety of the arc of relative movement of the arms, preferably through intermeshing gear sectors formed at their proximal ends.

The hinge plate is provided with a plurality of adjustment apertures arranged in an angularly spaced apart pattern for reception of a pair of limit pins to intercept rotation along the arc of rotation of at least one of the arms, thereby to limit rotation of both of the arms.

The proximal end portion of the one arm includes an extension facing edge and a flexion facing edge, the extension facing edge being adapted to engage a limit pin in the direction of extension movement and the flexion facing edge being adapted to engage a second limit pin in the direction of flexion movement. The pins, extending through the apertures into which they are inserted, thus restrain movement of the arm beyond the positions defined by the respective limit pins.

Adjustment of the permitted range of motion is obtained by repositioning the pins from one aperture to another to adjust the arc of rotation of the pair of arms, preferably in 15° or 30° increments, between a final extension position and a final flexion position. In the preferred embodiment, each of the apertures is labeled according to its specific angular position for extension or flexion, further promoting convenient adjustment.

By appropriate positioning of the pair of limit pins, the hinge may accommodate the full 180° range of relative motion between the two arms, or any range of motion within the 180° arc. Alternatively, the two arms can be locked, in 15° or 30° increments of angular adjustment, in any position between full extension and full flexion.

In the preferred embodiment, strength and durability are promoted by use of a pair of parallel spaced apart hinge plates, positioned on opposite sides of the proximal, interengaging ends of the rigid support arms. The pair of hinge plates thus overlie and cover the proximal ends of the arms and prevent entry of foreign objects and/or the wearer's skin between the arms. The two hinge plates are preferably provided with aligned adjustment apertures and the limit pins extend between and are supported by both plates, thereby firmly restraining the arms from movement past the limit pins. Additionally, for added strength, adjustment apertures are formed in the hinge plates about both pivot pins and two pairs of limit pins are provided so that there are two pins to limit movement in each of the two directions of relative movement of the arms.

Additionally, an openable cover member, specifically a flip-top cap, is provided to allow selective access to the limit pins for purposes of adjustment and to normally overlie the pins and prevent inadvertent or accidental displacement of the pins from their intended positions of adjustment.

Reliability is enhanced by securing each of the limit pins to the respective pivot pin through a retaining means or tether. The tether is comprised of an elastomeric strap which carries the limit pin at one of its ends and which is pivotally mounted at its other end on the respective pivot pin thereby to allow pivotal movement of the tether and the limit pin about the axis of the pivot pin. The tether is also provided with an orifice, preferably a radial slot, to permit movement of the limit pin radially relative to the hinge plate thereby to facilitate alignment of the limit pin with every aperture location on the hinge plate. The tethers thereby retain the limit pins against loss or misplacement, while at the same time allowing the limit pins to be readily repositioned among the adjacent apertures. The tether is provided with a window opening to allow observation of aperture labels during the adjustment process.

The support arms and hinge plates of the hinge of the invention are designed so that the same can be conveniently and economically stamped out of sheet metal stock, e.g., aluminum or stainless steel stock, thereby providing an extremely durable hinge at a very economical price.

These and other objects and advantages of the invention will become apparent from the following detailed description, as considered in conjunction with the accompanying drawings.

DETAILED DESCRIPTION

The following is a detailed description of the embodiments of the invention presently contemplated by the inventor to be the best mode of carrying out his invention.

Referring to FIGS. 1 through 4, a first embodiment 10 of the orthopaedic polycentric hinge of the invention is comprised of a pair of rigid support arms 12, 14 juxtaposed to one another at adjacent or proximal ends and which, in relation to the knee of the patient, have forwardly facing edges 12a, 14a and rearwardly facing edges 12b, 14b. The two support arms 12, 14 are pivotally interconnected at their proximal ends by a hinge assembly 16, comprised preferably of a pair of parallel, spaced apart rigid hinge plates 18, 20 overlying the opposite sides, i.e., the exterior and interior sides respectively, of the proximal ends of the support arms 12, 14 and which are pivotally connected to and pivotally interconnect the proximal ends of the arms 12, 14. The hinge plates 18, 20 define therebetween a space 21 within which rotation of the arms 12, 14 may occur.

The hinge plates 18, 20 are secured to one another and are pivotally connected to the arms 12, 14 by means of a pair of pivot pins or rivets 22 and 24 respectively. The hinge plates 18, 20 and pivot pins 22, 24 thereby connect the proximal ends of the support arms 12, 14 for relative rotation about a pair of spaced parallel axes in a motion that closely approximates the movement accommodated by the human knee joint.

As illustrated in the drawings, the hinge will be oriented for attachment to the inner or medial side of the right knee and the outer or lateral side of the left knee when the arm 12 is affixed to the upper leg and the arm 14 is affixed to the lower leg, and will be oriented for attachment to the outer or lateral side of the right knee and the inner or medial side of the left knee when the arm 12 is affixed to the lower leg and the arm 14 is affixed to the upper leg. In either orientation, one of the support arms is secured to the upper leg or thigh of the patient above the injured knee and the other support arm is secured to the lower leg or calf below the knee, with the polycentric hinge properly aligned along side the knee. Depending upon the severity of the injury and the degree of support required, the knee may be supported by a single brace on one side of the knee or by a pair of braces located respectively on opposite sides of the knee.

Various means of affixing the support arms to the upper and lower legs of the patient are disclosed in the prior art, for example, U.S. Pat. Nos. 3,786,804, 3,817,244, 4,088,130, 4,361,142, 4,372,298, 4,407,276, 4,493,316 and 4,628,916. To accommodate attachment of the securing means to the brace, holes 12e–12h and 14e–14h are preferably provided in the arms 12 and 14.

The length of each arm 12, 14 between its proximal and distal ends is a matter of choice, but a preferred length is in the order of about 8 inches with a leg engaging portion of about 6½ inches and a proximal end or hinge portion of about 1½ inches. The width of each support arm 12, 14 is preferably in the order of about 1 inch or slightly more, with a thickness of about ⅛ inch.

As illustrated, the hinge plates 18, 20 are preferably generally curvilinearly shaped on their side edges along a pair of arcs coincident respectively with the arcs of pivotal movement of the arms 12, 14. The hinge plates 18, 20 are preferably identical to one another.

Figure 3:
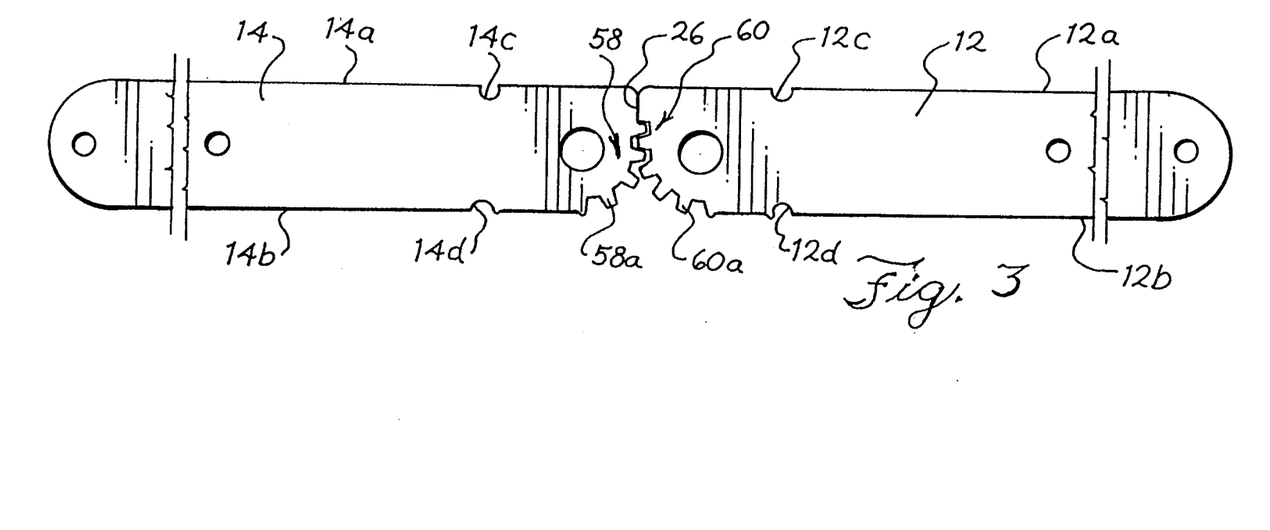
FIG. 3 is a plan view of the proximal ends of the rigid support arms of the first embodiment of the invention with the hinge plates removed and showing the complementary and interlocking arcuate surfaces of the arms.
Figure 4:
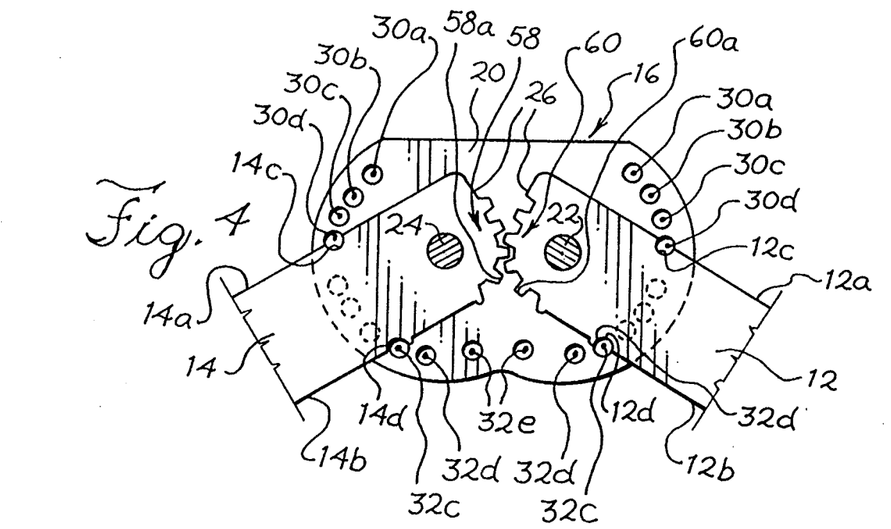
FIG. 4 is a plan view of the proximal ends of the rigid support arms and one of the hinge plates of the first embodiment of the invention and showing the relationship between the support arms and the adjustment means provided on the hinge plate.

Referring to FIGS. 3 and 4, the proximal end surfaces of the two support arms comprise complementary, mutually engaging surfaces formed on arcs of curvature conforming to the polycentric movement between the arms 12, 14, so that the two arms engage one another and derive mutual support and guidance one from the other throughout substantially the entirety of the arc of relative rotation of the arms. Consequently, forces imparted to the hinge 10 in the plane of the hinge are borne by the entirety of the hinge construction, including the abutting surfaces of the support arms, so that the integrity of the hinge 10 is not reliant solely on the hinge plates 18, 20 and the pivot pins 22, 24.

Further, to provide for continual inter-engagement of the components of the hinge for maintaining the same in predetermined engaged relationship with one another, the mutually engaging end surfaces of the arms are provided with respective sets of gear teeth 58, 60, the teeth of which are intermeshed and engaged with one another in all positions of relative rotation between the arms. To accommodate relative rotation of the arms to a position of complete flexion while maintaining the interlocking relationship, the flexion direction terminal ends of the mutually engaging surfaces include gear teeth 58a, 60a, respectively, which extend onto the rearwardly facing edges 12b, 14b of the arms and maintain the intermeshed relationship between the gear teeth even in the position of full flexion. Consequently, the relationship of the components of the hinge one to another is permanently fixed and unchanging in each and every position of relative rotation between the arms. Also, the proximal, mutually engaging surfaces of the support arms 12, 14 are provided adjacent their forwardly facing edges 12a, 14a with abutment surfaces 26 which, in the direction of relative rotation toward the position of knee/leg extension prevent rotation beyond a substantially aligned, nearly upright, extended position. This arrangement insures that the knee of the patient cannot move into a position where there may be a potential for or a likelihood of traumatization of the knee, especially undesired hyperextension.

Figures 1, 8:
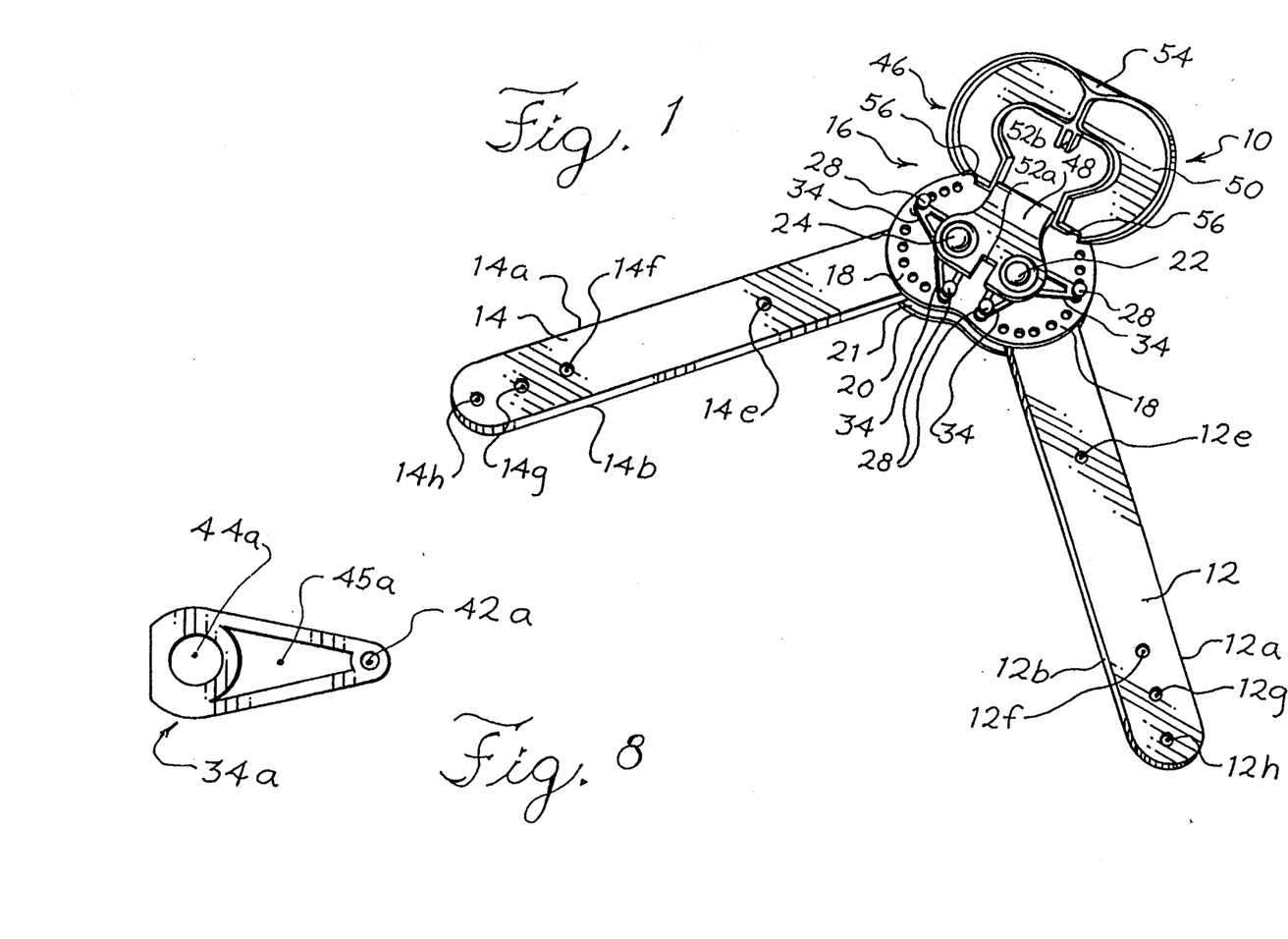
FIG. 1 is a perspective view of a first embodiment of the polycentric hinge of the present invention in a partially extended position, the view showing the hinge assembly with the cover opened to expose the adjustment means.
FIG. 8 is a plan view of a first embodiment of a limit pin retainer.
Figures 5, 6:
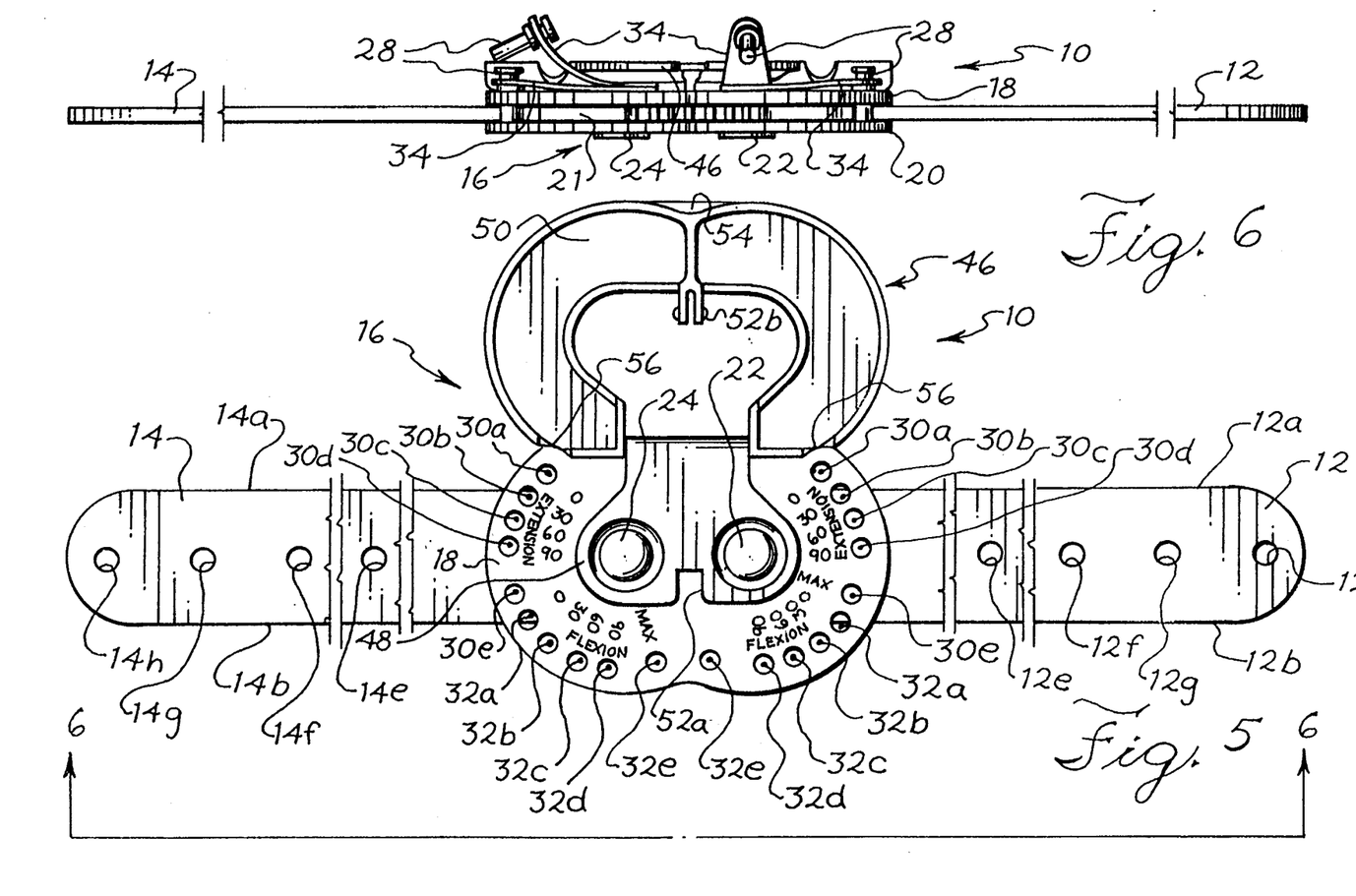
FIG. 5 is a plan view of the first embodiment of the invention showing the hinge assembly with the cover opened and with the limit pins and limit pin retainers omitted for purposes of illustration of the markings or labels preferably provided on the exposed one of the hinge plates.
FIG. 6 is a side elevation of the first embodiment of the invention taken along the line 6—6 of FIG. 5.

For injured or injury-prone knees that should not be permitted a normal range of movement, further protection is provided by range of motion adjustment means incorporated within the hinge assembly 16. As shown in FIGS. 1, 4 and 5, the hinge plates 18, 20 are provided with aligned pairs of angularly spaced limit stop receiving holes or apertures arranged concentrically about at least one and preferably both of the pivot pins 22 and 24. The limit stop receiving holes are arranged in respective sets 30a–30e for defining extension limit positions and sets 32a–32e for defining flexion limit positions. The holes or apertures are adapted for reception therein of limit pins 28, which in the preferred embodiment are four in number, two for insertion in corresponding pairs of the two sets of extension limit holes 30a–30e and two for insertion in corresponding pairs of the two sets of flexion limit holes 32a–32e. While desired limits of extension and flexion could be established by a single set of extension limit holes 30 and a single set of flexion limit holes 32 and the use of just two limit pins 28, the use of four sets of holes and four pins effectively doubles the strength of the motion limiting means, thereby to provide a very sturdy construction having a large number of limit positions without necessitating large or heavy duty limit stop pins and fewer limit positions.

The pins 28 are situated to be engaged by extension abutment means 12c, 14c and flexion abutment means 12d, 14d, shown as semi-circular recesses in each of the arms 12, 14. In the first embodiment, the apertures in each set are located at substantially equal angular intervals along an arc concentric with the axis of rotation of the respective one of the arms. The limit pins 28 inserted in corresponding ones of the adjustment apertures 30a–30e thus establish an adjustable range of relative arm rotation for extension, while the limit pins 28 inserted in corresponding ones of the adjustment apertures 32a-32e establish an adjustable range of relative arm rotation for flexion.

Each limit pin 28 is of a size and shape to pass through the selected aperture in the hinge plate 18 and to extend into the space 21 between the hinge plates to act as a barrier and limit further rotation of the arms in a given direction, i.e., by engagement therewith of the extension abutment means 12c, 14c or the flexion abutment means 12d, 14d. In the preferred embodiment, the limit pins 28 are of a length to extend through the space 21 and engage within corresponding aligned adjustment apertures provided in and through the hinge plate 20, thereby protecting the limit pins from bending or jamming.

For convenience and accuracy of use, each of the extension apertures 30a-30e and each of the flexion apertures 32a-32e is marked or labeled as shown in FIG. 5 to designate the operative angular limitations selected by insertion of the limit pins. Preferably, the adjustment apertures 30a-30e, 32a-32e are arranged at regular intervals of 30°, which is generally sufficient to accommodate the various ranges of knee flexure desired.

To demonstrate the convenient adjustment of the range of knee movement accommodated by the hinge assembly 16, reference is made to FIG. 1 wherein extension limit pins 28 are placed in extension apertures 30d, for example, and flexion limit pins 28 are inserted in flexion apertures 32e. With the limit or stop pins in these positions, the arms 12 and 14 can be moved from a position of maximum flexion, wherein the arms are in substantially side-by-side parallel relation, to a position approximately half-way extended wherein the arms define an angle of about 90° between them. For this reason, the holes or apertures 30d are appropriately marked or labeled "90" as illustrated in FIG. 5. By moving the extension limit pins, for example, to holes 30c, an additional 30° of movement in extension is accommodated, i.e., to a position wherein the extension angle limit is about 60° from full extension. Further, by moving the extension limit pins to the holes 30a, full or complete extension is accommodated. In the latter position, as above described, hyperextension is prohibited by virtue of engagement of the abutment surfaces 26 on the ends of the arms 12, 14.

In similar fashion, the degree of knee flexion accommodated by the brace is readily adjusted by selective positioning of the flexion limit pins in the flexion limit holes or apertures 32a-32e. For example, by placing the extension limit pins in holes 30b and by inserting the flexion limit pins in holes 32d, both extension and flexion would be limited to 60° of total relative arm rotation. Consequently, by appropriate positioning of the pins 28 in the holes or apertures, limits can be established on the permissible degree of each of knee extension and knee flexion, and desired ranges of knee motion can be established.

Moreover, by appropriate positioning of the limit or stop pins 28, the hinge can be locked in any desired fixed position of adjustment. For example, with reference to FIG. 5, with the extension limit pins inserted in holes 30a and the flexion limit pins inserted in holes 32a, the hinge will be locked in a position of full extension; with the pins in holes 30d and 32d the hinge will be locked in its 90° position; and with the arms substantially side-by-side and pins positioned in holes 32a, the hinge will be locked in a position of full flexion.

Thus, the hinge of the invention provides for universal adjustability of a rehabilitative knee brace.

Figure 7:
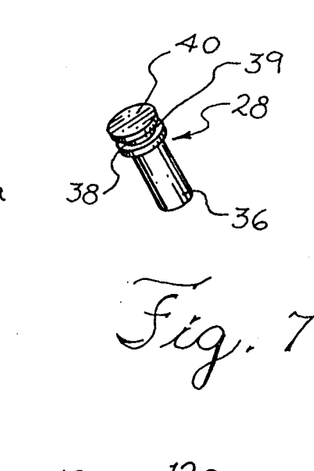
FIG. 7 is a perspective view of one of the limit pins.

As shown in FIGS. 1 and 6, each limit pin 28 is retained in association with the hinge assembly 16 by a retainer means or tether 34. As shown in detail in FIG. 7, each limit pin 28 includes a shank 36, a collar 38, a tether receiving portion 39 and a head 40. Both the collar 38 and head 40 have an outer diameter greater than that of the shank 36 and the portion 39, and also greater than the diameter of the pin receiving adjustment holes 30a-30e, 32a-32e. One embodiment 34a of a limit pin retainer or tether 34 is shown in FIG. 8 as comprising a flexible strap, suitably formed from a polymeric material, having a hole 44a therethrough for passage of a respective one of the pivot pins 22 and 24 during assembly of the hinge, and a limit pin receiving orifice 42a having an inner diameter slightly greater than the outer diameter of the tether receiving portion 39, but smaller than the outer diameters of the collar 38 and head 40 of the limit pin. Situated between the orifices 42a and 44a is an opening or window 45a, which allows for viewing of the labeling of the apertures on the plate 18 to promote convenient adjustment of the limit pin locations. Each limit pin 28 is inserted into the limit pin orifice 42a of a respective one of the retainers, with the retainer trapped between the collar 38 and head 40 of the pin so that the pin is securely attached to the retainer. Two of the retainers are pivotally mounted on each of the pivot pins to properly locate the respective pairs of limit pins. The distance between the apertures 42a and 44a is substantially the same as or slightly greater than the distance between the adjustment apertures 30a-30e, 32a-32e and the respective pivot pin to facilitate insertion of the limit pins into the apertures while firmly and safely retaining the pins in association with the hinge. Thus, the limit pins 28 can be readily removed from one aperture and pivotally moved for relocation to another aperture without fear of the limit pins being lost or misplaced.

Other embodiments of limit pin tethers or retainers will be described later herein with reference to FIGS. 9-11.

Figures 9, 12:
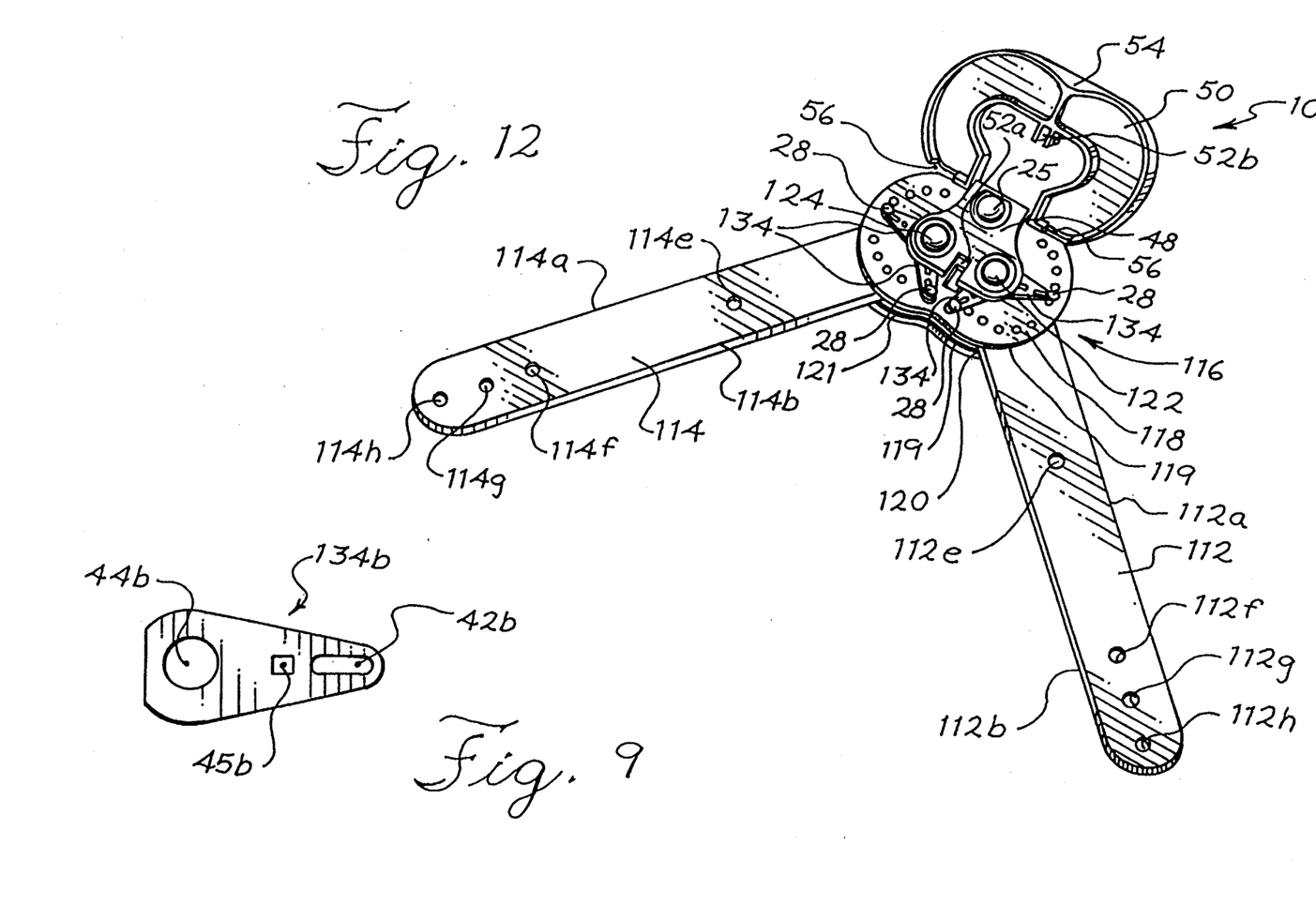
FIG. 9 is a plan view of a second embodiment of a limit pin retainer.
FIG. 12 is a perspective view of a second embodiment of the polycentric hinge of the invention in a partially extended position and with the cover opened to expose the adjustment means.
Figure 14:
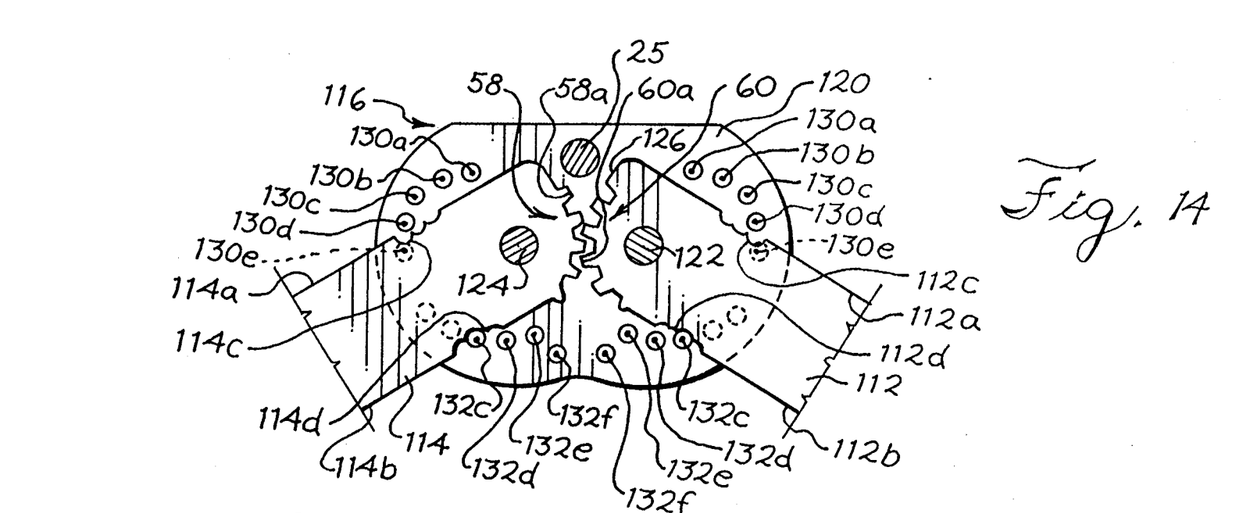
FIG. 14 is a plan view of the proximal ends of the rigid support arms and one of the hinge plates of the second embodiment of the invention and showing the relationship between the support arms and the adjustment means provided on the hinge plate.

Referring now to FIGS. 12 and 14, a second embodiment of the orthopaedic polycentric hinge of the present invention is disclosed as being comprised of components quite similar to the components of the first embodiment. Due to the similarity, elements of the second embodiment the same as or similar to corresponding elements of the first embodiment are indicated by the same reference numerals and/or corresponding reference numerals in the 100 series.

As shown, the second embodiment is also comprised of a pair of rigid support arms 112, 114 having forwardly facing edges 112a, 114a and rearwardly facing edges 112b, 114b. A pair of parallel, spaced apart rigid hinge plates 118, 120 overlie the opposite sides of the proximal ends of the arms and a pair of pivot pins 122, 124 pivotally interconnect the hinge plates and the proximal ends of the arms to form a hinge assembly 116. The hinge plates 118, 120 define therebetween a space 121 within which rotation of the arms 112, 114 may occur. To promote freedom of rotary movement, a thin layer 119 of nylon or teflon is placed between the interior surface of each of the hinge plates 118, 120 and the contiguous surfaces of the proximal ends of the arms 112, 114. Each layer 119 preferably follows the shape of the hinge plates 118, 120. Nylon or teflon washers may be used as an alternative if desired.

The hinge plates 118, 120 and pivot pins 122, 124 thus connect the proximal ends of the rigid support arms 112, 114 for pivotal movement about a pair of spaced parallel axes in a motion closely approximating the motion of the human knee joint.

As in the first embodiment, the proximal end surfaces of the two support arms have complementary, mutually engaging surfaces formed on arcs of curvature conforming to the movement accommodated between the arms. The end surfaces are preferably provided with intermeshing gear teeth and the end surfaces engage one another to derive mutual support and guidance one from the other throughout substantially the entirety of the arc of relative rotation accommodated between the arms. Abutment surfaces 126 prevent relative rotation of the arms beyond a substantially aligned, nearly upright, extended position, thereby to prohibit hyperextension of the knee.

Range of motion adjustment means comprised of four limit pins 28 and respective sets of extension adjustment apertures 130a–130e and flexion adjustment apertures 132a–132f are again incorporated in the hinge plates 118, 120.

In contrast to the first embodiment, the adjustment apertures 130, 132 are not located along circular arcs concentric with the respective axes of rotation of the arms, but rather are set in a pattern only generally following the arc of rotation of the arms. For example, extension adjustment aperture 130a is located closer to the respective pivot pin 122 or 124 than aperture 130b, and both are located closer to the pivot pin than aperture 130c. In similar fashion, flexion adjustment aperture 132e is located closer to the respective pivot pin than aperture 132d, and both are located closer to the pivot pin than aperture 132f. By employing this aperture orientation, a full range of adjustments can be accommodated with particular accuracy and without impairing the strength and integrity of the hinge plates.

Figures 15, 16:
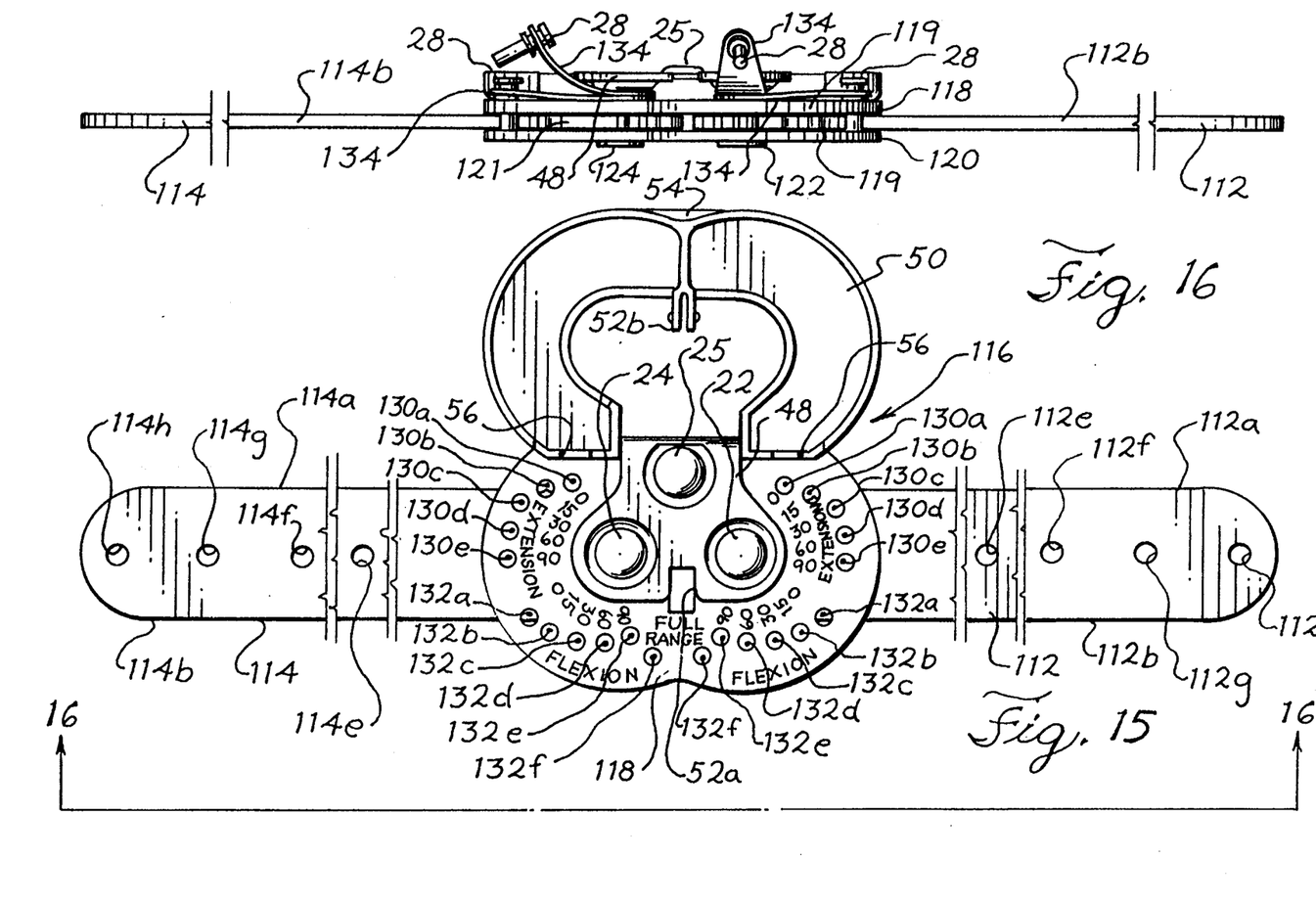
FIG. 15 is a plan view of the second embodiment of the polycentric hinge of the invention showing the hinge assembly with the cover opened and with the limit pins and limit pin retainers omitted for the sake of clarity.
FIG. 16 is a side elevation of the second embodiment of the hinge taken along line 16—16 of FIG. 15.

Each of the extension apertures 130a–130e and each of the flexion apertures 132a–132f are labeled on the exposed surface of the hinge plate 118, as shown in FIG. 15, to designate the operative angular limitations obtained upon insertion of the limit pins. Preferably, the adjustment apertures 130a–130e, 132a–132f are arranged at intervals of 15° or 30° to accommodate a wide range of knee flexure adjustments.

Figure 13:
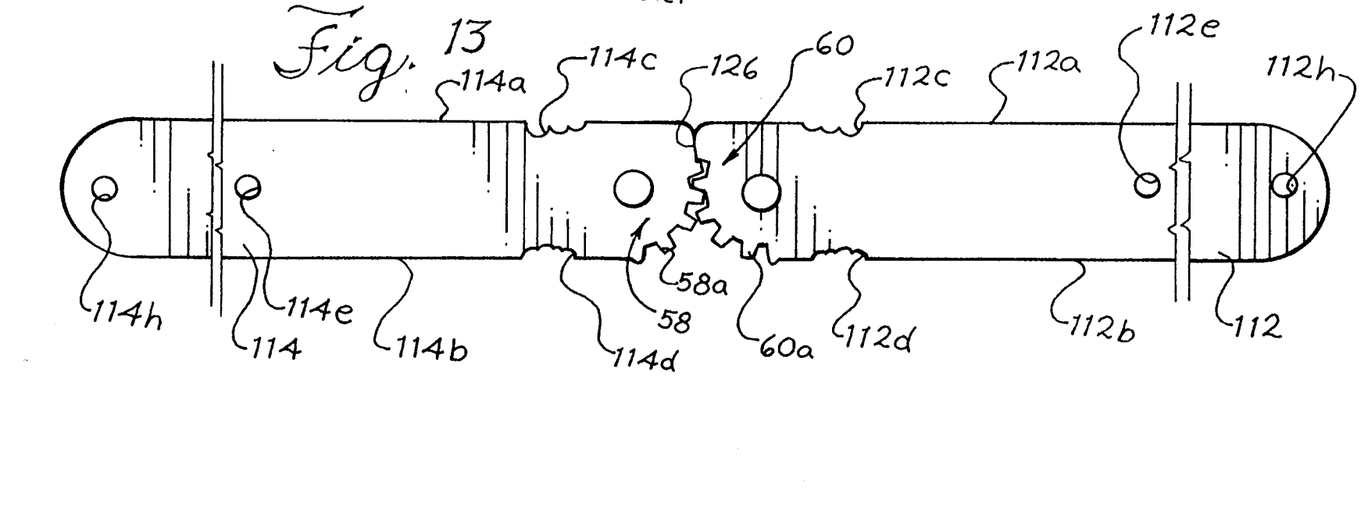
FIG. 13 is a plan view of the proximal ends of the rigid support arms of the second embodiment of the invention with the hinge plates removed.

As shown in FIGS. 13 and 14, the arms 112, 114 are provided with limit pin abutment means 112c, 114c, 112d, 114d comprising multi-faceted abutment surfaces formed in and located along the sides of the arms so as to intercept the limit pins 28 in all adjustment positions established by apertures 130a–130e, 132a–132f. Various abutment surfaces can be employed, depending on the particular aperture orientation selected.

Because the limit pin apertures 130a–130e, 132a–132f in the second embodiment of the hinge are not all located at equal radial distances from the axis of the respective pivot pin, it is desirable to provide a tether 134 for each limit pin that will be effective to retain the limit pin permanently in association with the hinge and that will also accommodate movement of the limit pin radially as well as angularly relative to the respective pivot pin. A number of retainers or tethers suitable for the purpose are shown in FIGS. 9 to 11.

Referring to FIG. 9, a flexible plastic tether 134b is provided with a limit pin receiving orifice 42b and pivot pin receiving orifice 44b. The tether is adapted to be pivotally affixed to the hinge by passage of the respective pivot pin through orifice 44b. The limit pin receiving orifice 42b is a radially elongated slot with a width slightly greater than the outer diameter of the pin tether engaging portion 39, but smaller than the outer diameters of the collar 38 and head 40, of the limit pin. The limit pin is inserted in the slot so that the portion 39 is slidably received in the slot and the collar 38 and head 40 prevent disassociation of the pin from the tether. The length of the tether and of the orifice 42b in the tether allow the limit pin to be moved radially toward and away from the respective pivot pin thereby to accommodate insertion of the limit pin into limit adjustment apertures that are spaced different radial distances from the pivot pin axis. An opening or window 45b is preferably provided in the tether 134b between the orifices 42b and 44b to accommodate viewing of the adjustment aperture labels on the adjacent hinge plate 118.

Figure 10:
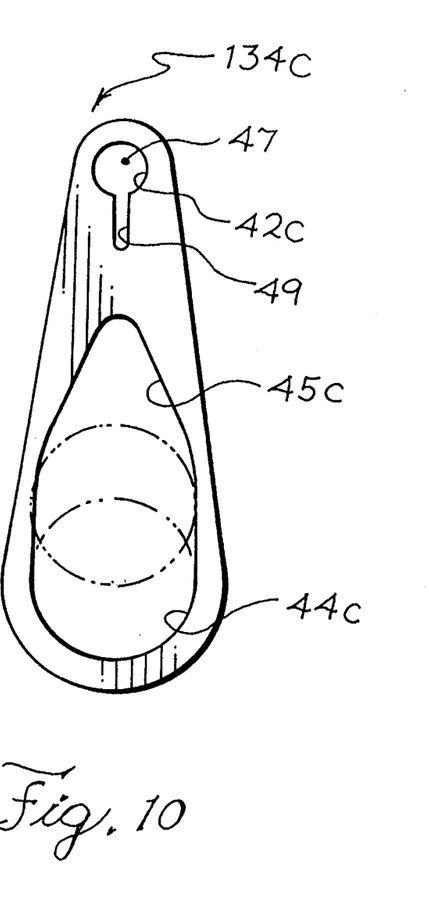
FIG. 10 is a plan view of a third embodiment of a limit pin retainer.

A second embodiment of a tether accommodating radial movement of the associated limit pin is shown in FIG. 10. In this embodiment, the tether 134c includes a limit pin receiving orifice 42c and a pivot pin receiving orifice 44c. The limit pin receiving orifice 42c includes a generally circular portion 47 and an adjoining slit 49 which facilitates insertion of the pin and passage of the retaining collar 38 through the tether. As shown in FIG. 10, the pivot pin orifice 44c is oversized—that is, it is elongated so as to form a radial slot longer than the outer diameter of the respective pivot pin. The slotted orifice 44c thus allows the tether 134c to both pivot about and move radially relative to the pivot pin so that the coupled limit pin 28 can be moved radially to accommodate aperture positions at varying distances from the axis of the pivot pin, as is indicated by the dotted lines in FIG. 10. Also forming a portion of the orifice 44c is a triangularly shaped opening or window 45c to accommodate viewing of the labeling of the adjustment apertures.

Figure 11:
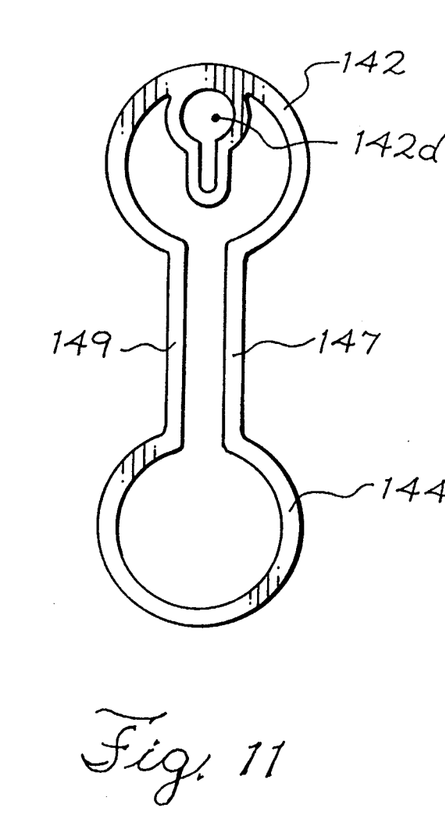
FIG. 11 is a plan view of a fourth embodiment of a limit pin retainer.

A third embodiment of a tether accommodating radial movement of the associated limit pin is illustrated at 134d in FIG. 11 as being comprised of a narrow, continuous, plastic, e.g., nylon, band formed as two nearly complete circles 142 and 144 joined together by short spaced parallel portions 147, 149 of the band. One circle 144 is adapted to be looped about a respective pivot pin of the hinge, thereby to pivotally mount the tether on the hinge. The other circle, at a point opposite the parallel joining portions, is provided with an integral tab having a hole 142d through it, and the limit pin is inserted through the hole. The circles are of a size such that, in the relaxed condition of the tether, the limit pin aligns itself at some predetermined radial distance from the pivot pin, for example, the radially innermost of the limit holes, and the retention member is stretchable to convert the circles to radially extended ellipses enabling the limit pin to be aligned with the radially outermost limit hole. The retention member thus performs much the same as a rubber band, without the short life-cycle limitations of a rubber band. Alternatively, the two circles of the retention member could be of a size such that, in the relaxed condition, the limit pin would be aligned with the outermost hole and the member could be compressed to convert the circles to arcuately extended ellipses enabling the limit pin to be aligned with the innermost hole.

Thus, the pin tethers or retention members illustrated in FIGS. 9–11 are effective to pivotally connect the limit pins to the hinge pivot pins for both arcuate and radial movement so that the limit pins can be moved to different arcuately and radially spaced adjustment apertures or holes without becoming disassociated from the hinge, i.e., without being lost or misplaced.

In the preferred embodiments of the invention, the limit or stop pins 28 are preferably sized so as to be easily and slidably insertable into and removable from the adjustment apertures or holes. Consequently, once the pins have been adjusted, it is desirable to provide a cover for the same so that they will not inadvertently become displaced from the selected holes. For this purpose, the present invention provides a novel and aesthetically attractive protective "flip-top" cover for the limit pins.

The pin cover of the invention, which is applicable to both the first and second embodiments of the hinge assembly and indicated generally at 46, is comprised of a base portion 48 and a "flip-top" cap 50 hingedly connected to the base portion 48 along one marginal edge of the hinge. The base portion 48 is secured to the outer surface or face of the hinge plate 18 or 118, respectively, through the pivot pins 22, 24 or 122, 124. In the second embodiment, an additional rivet 25 extends through the base portion 48 and the hinge plate 118 to more securely mount the cover 46 on the hinge assembly.

Figure 2:
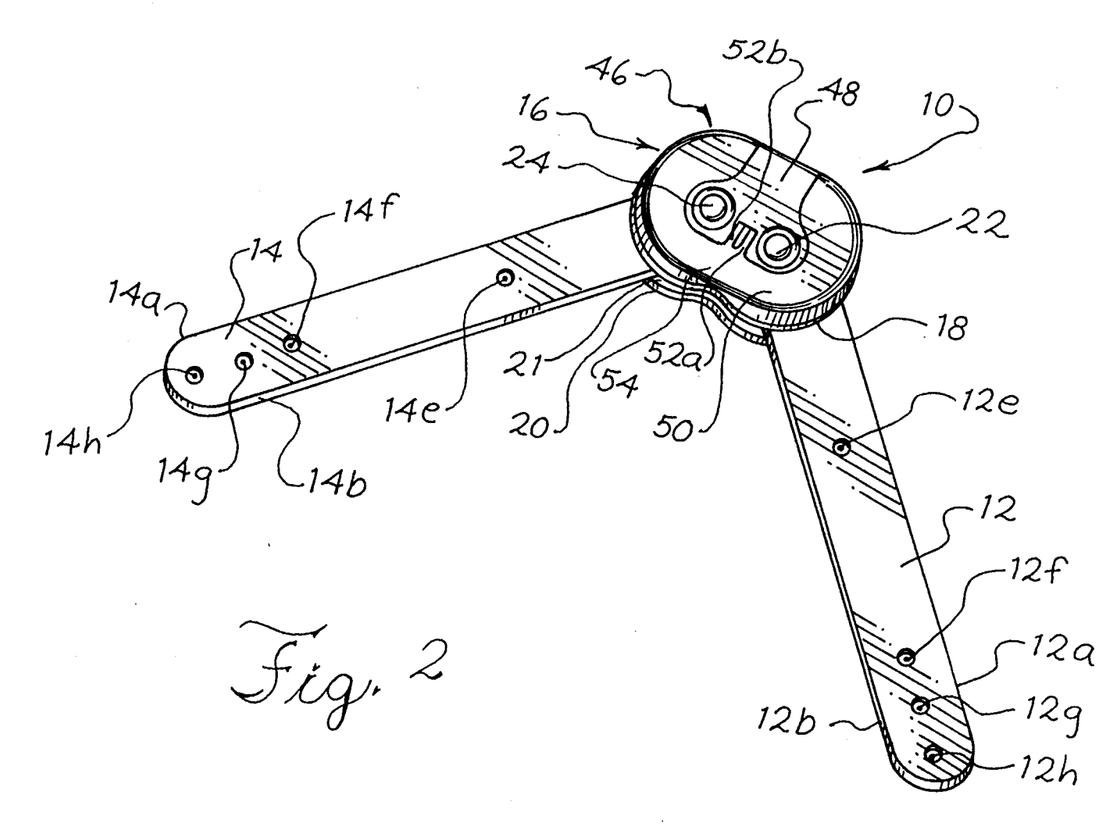
FIG. 2 is a perspective view of the first embodiment of the polycentric hinge of the present invention, also in the partially extended position, the view showing the hinge assembly with the cover closed.

The cap 50 preferably conforms closely to the curvilinear shape of the hinge plate 18 or 118, such that when closed, as shown in FIG. 2, the adjustment means is completely covered and protected from foreign objects, and the hinge assembly has a clean, neat and attractive appearance. When it is desired to manipulate the adjustment means, the cap 50 can be easily disengaged from cooperating resilient latching means 52a, 52b, on the base portion 48 and cap 50 respectively, and "flipped" open by a gentle force applied against a thumb tab 54. Conversely, the cap can readily be "flipped" back to a closed position and locked closed by reengagement of the latch means 52a, 52b. When the cap 50 is open, virtually the entire hinge plate 18 or 118 is exposed for inspection and pin adjustment as described above. A feature found desirable is the provision of a cutout 56 on either side of the cap 50 proximate the extension adjustment apertures 30a or 130a. This eliminates interference with movement of the cap when limit pins 28 are inserted in apertures 30a or 130a. Otherwise, the flip-top cap 50 completely encloses the adjustment means of the hinge assembly 16 or 116.

The invention thus provides a polycentric orthopaedic hinge of attractive appearance, sturdy construction and easy and precise adjustment over the full range of adjustments required for rehabilitative knee assistance or support. Nonetheless, the hinge can be manufactured very economically inasmuch as all four of the major components can be readily, quickly and economically fabricated from sheet metal stock, e.g. aluminum or stainless steel stock, by stamping the same out of intermittently fed sheet metal stock purchased in roll or coil form. The limit pins 28 are also readily fabricated and the tethers 34 and cover 46 can be manufactured from various elastomeric and rigid polymers, respectively, using any number of methods. Further, the assembly of the components is quickly and economically achieved by means of only a few rivets.

The objects and advantages of the invention have thus been shown to be attained in a convenient, practical, economical and facile manner.

While preferred embodiments of the invention have been herein illustrated and described, it is to be appreciated that various changes, rearrangements and modifications may be made therein without departing from the scope of the invention as defined by the appended claims.

What is claimed is:

1. A polycentric hinge for orthopaedic braces having a hinge plate, a pair of support arms, and a pair of pivot pins pivotally connecting the support arms to the hinge plate on spaced parallel axes,
   a first set of extension limit apertures in the hinge plate spaced angularly about one of the pivot pins,
   a second set of extension limit apertures in the hinge plate spaced angularly about the other pivot pin,
   a first set of flexion limit apertures in the hinge plate spaced angularly about said one pivot pin,
   a second set of flexion limit apertures in the hinge plate spaced angularly about said other pivot pin,
   a first separate, individually and independently adjustable extension limit pin selectively insertable in the extension limit apertures of the first set of extension limit apertures,
   a second separate, individually and independently adjustable extension limit pin selectively insertable in the extension limit apertures of the second set of extension limit apertures,
   said extension limit pins governing pivotal movement of the arms in extension,
   a first separate, individually and independently adjustable flexion limit pin selectively insertable in the flexion limit apertures of the first set of flexion limit apertures,
   a second separate, individually and independently adjustable flexion limit pin selectively insertable in the flexion limit apertures of the second set of flexion limit apertures,
   said flexion limit pins governing pivotal movement of the arms in flexion,
   a first pair of flexible limit pin tethers pivotally mounted on said one pivot pin, one tether of said first pair extending from said one pivot pin to the first set of extension limit apertures and carrying said first extension limit pin, the other tether of said first pair extending from said one pivot pin to the first set of flexion limit apertures and carrying said first flexion limit pin,
   a second pair of flexible limit pin tethers pivotally mounted on said other pivot pin, one tether of said second pair extending from said other pivot pin to the second set of extension limit apertures and carrying said second extension limit pin, the other tether of said second pair extending from said other pivot pin to the second set of flexion limit apertures and carrying said second flexion limit pin,
   said tethers carrying said limit pins so that each limit pin is angularly movable and individually and independently adjustable about the respective pivot pin for selective insertion in the apertures of the respective set of apertures and is retained permanently associated with the respective pivot pin by the respective tether so as not to be lost or misplaced.

2. A hinge as set forth in claim 1 wherein the hinge plate bears aperture identifying labels adjacent the apertures in each set of apertures and each tether has a window opening therein through which the labels can be viewed to facilitate placement of the first and second extension limit pins in corresponding apertures of the first and second sets of extension limit apertures and to facilitate placement of the first and second flexion limit pins in corresponding apertures in the first and second sets of flexion limit apertures.

3. A hinge as set forth in claim 1 wherein the limit apertures in each set of apertures are spaced angularly about the respective pivot pin at different radial distances from the respective pivot pin and wherein each of said tethers accommodates both angular and radial movement of each of the limit pins relative to the pivot pins.

4. A hinge as set forth in claim 1 including a cover of a size and shape conformed substantially to the size and shape of the hinge plate for covering the hinge plate, the limit apertures and the limit pins and for retaining the limit pins in selected apertures, said cover being hingedly connected to the hinge plate adjacent a marginal edge of the hinge plate and on an axis parallel to the hinge plate, said cover being hingedly movable from a closed position overlying and covering the hinge plate, the limit apertures and the limit pins to an open position wherein the hinge plate and all of the limit apertures and all of the limit pins are exposed to accommodate simultaneous access to all of the limit pins and limit apertures.

5. A hinge as set forth in claim 4 wherein said cover includes means for releasably securing the same in its closed position.

6. A hinge as set forth in claim 4 wherein the hinge plate is shaped curvilinearly about the axes of the pivot pins and said cover is of substantially the same size and shape and conformably covers the hinge plate in the closed position.

7. A hinge as set forth in claim 4 wherein said cover comprises a base portion secured to the hinge plate by the pivot pins and extending to a marginal edge of the hinge plate and a cap hingedly mounted on said base portion at and parallel to said marginal edge.

8. A hinge for an orthopaedic brace having a pair of support arms, a hinge plate associated with the arms, at least one pivot pin for connecting the arms for pivotal movement relative to one another, pivotal movement limit apertures in the hinge plate, and a plurality of limit pins selectively insertable in the apertures to govern relative pivotal movement of the arms, and including a cover of a size and shape conformed substantially to the size and shape of the hinge plate for covering the hinge plate, the limit apertures and the limit pins and for retaining the limit ping in selected apertures;

said cover being hingedly connected to the hinge plate adjacent a marginal edge of the hinge plate and on an axis parallel to the hinge plate, said cover being movable from a closed position overlying and covering the hinge plate, the limit apertures and the limit pins to an open position wherein the hinge plate and all of the limit apertures and all of the limit pins are exposed to accommodate simultaneous access to all of the limit pins and limit apertures.

9. A hinge as set forth in claim 8 wherein said cover comprises a base portion secured to the hinge plate and extending to a marginal edge of the hinge plate and a cap hingedly mounted on said base portion adjacent to said marginal edge of and on an axis parallel to the hinge plate.

10. A hinge as set forth in claim 9 wherein said base portion and said cap include cooperable releasable latching means for releasably securing said cap in its closed position.

* * * * *